(12) United States Patent
Bielstein (10) Patent No.: US 9,916,436 B2
(45) Date of Patent: Mar. 13, 2018

(54) INTELLIGENT ACCESSORIES FOR MEDICAL DEVICES

(71) Applicant: Physio-Control, Inc., Redmond, WA (US)

(72) Inventor: Matthew L. Bielstein, Seattle, WA (US)

(73) Assignee: Physio-Control, Inc., Redmond, WA (US)

( * ) Notice: Subject to any disclaimer, the term of this patent is extended or adjusted under 35 U.S.C. 154(b) by 33 days.

(21) Appl. No.: 14/523,727

(22) Filed: Oct. 24, 2014

(65) Prior Publication Data

US 2016/0117496 A1 Apr. 28, 2016

(51) Int. Cl.
*A61N 1/372* (2006.01)
*G06F 21/44* (2013.01)
*A61N 1/39* (2006.01)

(52) U.S. Cl.
CPC ....... *G06F 21/445* (2013.01); *A61N 1/37235* (2013.01); *A61N 1/3925* (2013.01)

(58) Field of Classification Search
CPC .................................................... G06F 21/445
See application file for complete search history.

(56) References Cited

U.S. PATENT DOCUMENTS

| | | | |
|---|---|---|---|
| 5,321,392 A | 6/1994 | Skakoon et al. | |
| 5,697,955 A | 12/1997 | Stolte | |
| 5,702,431 A | 12/1997 | Wang et al. | |
| 5,721,482 A | 2/1998 | Benvegar et al. | |
| 5,939,856 A | 8/1999 | Demuro et al. | |
| 6,072,229 A | 6/2000 | Steijer et al. | |
| 6,072,299 A | 6/2000 | Kurle et al. | |
| 6,101,413 A | 8/2000 | Olson | |
| 6,127,063 A | 10/2000 | Kowalsky et al. | |
| 6,181,102 B1 | 1/2001 | Andrews et al. | |
| 6,223,077 B1 | 4/2001 | Schweizer et al. | |
| 6,246,907 B1 | 6/2001 | Lin | |
| 6,249,105 B1 | 6/2001 | Andrews et al. | |
| 6,291,966 B1 | 9/2001 | Wendelrup et al. | |
| 6,397,104 B1 | 5/2002 | Miller | |
| 6,438,415 B1 | 8/2002 | Powers | |
| 6,560,485 B2 | 5/2003 | Herliekson | |
| 6,639,381 B2 | 10/2003 | Tamura et al. | |

(Continued)

FOREIGN PATENT DOCUMENTS

| CN | 1859946 A | 11/2006 |
|---|---|---|
| KR | 1020040095307 A | 12/2004 |
| WO | 2006102420 A2 | 12/2006 |

OTHER PUBLICATIONS

International Preliminary Report on Patentability, Patent Cooperation Treaty, dated Dec. 2, 2010, 11 pages, PCT/US2009/045943, European Patent Office.

(Continued)

*Primary Examiner* — Joseph Dietrich
(74) *Attorney, Agent, or Firm* — Lane Powell, PC (57) ABSTRACT

An accessory for a host medical device that is capable of authenticating itself to the host medical device. The accessory includes an onboard facility for authenticating the accessory to the host medical device. Various embodiments of the accessory enable it to validate itself to the host medical device without the host medical device reading any stored information from the accessory.

28 Claims, 7 Drawing Sheets

(56) References Cited

U.S. PATENT DOCUMENTS

| | | |
|---|---|---|
| 6,690,959 B2 | 2/2004 | Thompson |
| 6,873,133 B1 | 3/2005 | Kavounas |
| 6,972,542 B2 | 12/2005 | Patino et al. |
| 7,095,210 B2 | 8/2006 | Tamura et al. |
| 7,250,612 B2 | 7/2007 | Pai-Paranjape et al. |
| 7,689,278 B2 | 3/2010 | Jonsen |
| 7,728,548 B2 | 6/2010 | Daynes et al. |
| 7,912,543 B2 | 3/2011 | Vaisnys |
| 8,185,196 B2 | 5/2012 | Vaisnys |
| 8,185,197 B2 | 5/2012 | Vaisnys |
| 8,229,562 B2 | 7/2012 | Ginggen et al. |
| 8,265,748 B2 | 9/2012 | Liu |
| 8,280,506 B2 | 10/2012 | Vaisnys |
| 8,406,874 B2 | 3/2013 | Liu |
| 8,774,916 B2 | 7/2014 | Vaisnys |
| 2003/0195581 A1 | 10/2003 | Meadows et al. |
| 2004/0039257 A1 | 2/2004 | Hickle |
| 2004/0049685 A1* | 3/2004 | Jaloveczki ............... G06F 21/36 713/182 |
| 2005/0113877 A1* | 5/2005 | Spinelli .............. A61N 1/36007 607/39 |
| 2006/0178170 A1 | 8/2006 | Chung et al. |
| 2006/0259081 A1 | 11/2006 | Vaisnys |
| 2007/0112389 A1 | 5/2007 | Jonsen |
| 2007/0143864 A1 | 6/2007 | Cabana et al. |
| 2008/0077185 A1 | 3/2008 | Pearce et al. |
| 2008/0140163 A1 | 6/2008 | Kreacher et al. |
| 2009/0187225 A1 | 7/2009 | Vaisnys |
| 2009/0233458 A1 | 9/2009 | Vaisnys |
| 2010/0168811 A1 | 7/2010 | Vaisnys |
| 2010/0174332 A1 | 7/2010 | Vaisnys |
| 2010/0198286 A1 | 8/2010 | Neumiller et al. |
| 2010/0198287 A1 | 8/2010 | Neumiller et al. |
| 2012/0197324 A1* | 8/2012 | Nova .................... A61N 1/3931 607/4 |
| 2013/0066389 A1 | 3/2013 | Vaisnys |

OTHER PUBLICATIONS

Response to Written Opinion for PCT/US2009/045943 filed Aug. 2, 2010.
International Search Report, Patent Cooperation Treaty, May 3, 2010, 4 pages, PCT/US2009/045943, European Office Patent.
Written Opinion, Patent Cooperation Treaty, Dec. 2, 2010, 6 pages, PCT/US2009/045943, European Patent Office.

\* cited by examiner

| Row | Secret | Date | Model | Features | Other |
|-----|--------|------|-------|----------|-------|
| 301 | u8vniicm4vu9tcioec | Oct 2014 | 0001 | XYZ | |
| 302 | 643d7cufdijxo493f | Nov 2014 | 0001 | DCU | |
| 303 | 4nyutcxmiodo4uct | Dec 2014 | 0001 | XYZ | |
| 304 | cn4uim894u5ti c4i | Jan 2015 | 0001 | XYZ | |
| 305 | 43cnu6voirkljbz7g | Feb 2015 | 0001 | XYZ | |
| 306 | 94cm0m0viokid6juy | Mar 2015 | 0001 | XYZ | |
| 307 | etxrcvvdb87fiun6o | Mar 2015 | 0002 | XYZ | |
| 308 | 7oimerpogj49085w | Mar 2015 | 0002 | DCU | |
| 309 | 5uijrcnjgkl3iohgjox | Apr 2015 | 0001 | XYZ | |

INTELLIGENT ACCESSORIES FOR MEDICAL DEVICES

TECHNICAL FIELD

The disclosed subject matter pertains to the area of medical devices, and more specifically to the area of medical devices and accessories for medical devices.

BACKGROUND INFORMATION

The use of field-deployed medical devices, such as portable defibrillators, is achieving widespread acceptance. Such devices are used to help provide critical medical treatment to patients as close to the time of need as possible. Because of their use in medical emergencies, such medical devices are subject to regulatory approval. Such medical devices are designed, tested, and approved as a system. However, some of the medical devices may include consumable components or components that have a limited life and must be replaced. Because proper operation and regulatory approval is contingent upon the system being configured properly, it may be important that such components be replaced with authorized replacements that are proper for the medical device.

SUMMARY OF EMBODIMENTS

Disclosed is a system for providing intelligent accessories, which may be used as replacement components of a host medical device. In certain embodiments, a medical device accessory is configured with an onboard processor, which performs computations to authenticate the accessory to the host medical device. In addition, the onboard processor may evaluate and report other characteristics of the accessory to ensure that it is the proper accessory for the host medical device.

DETAILED DESCRIPTION

Generally described, embodiments are directed to an accessory for a host medical device that is capable of authenticating itself to the host medical device. The accessory includes an onboard facility for authenticating the accessory to the host medical device. Various embodiments of the accessory enable it to validate itself to the host medical device without the host medical device reading any stored information from the accessory.

Figure 1:
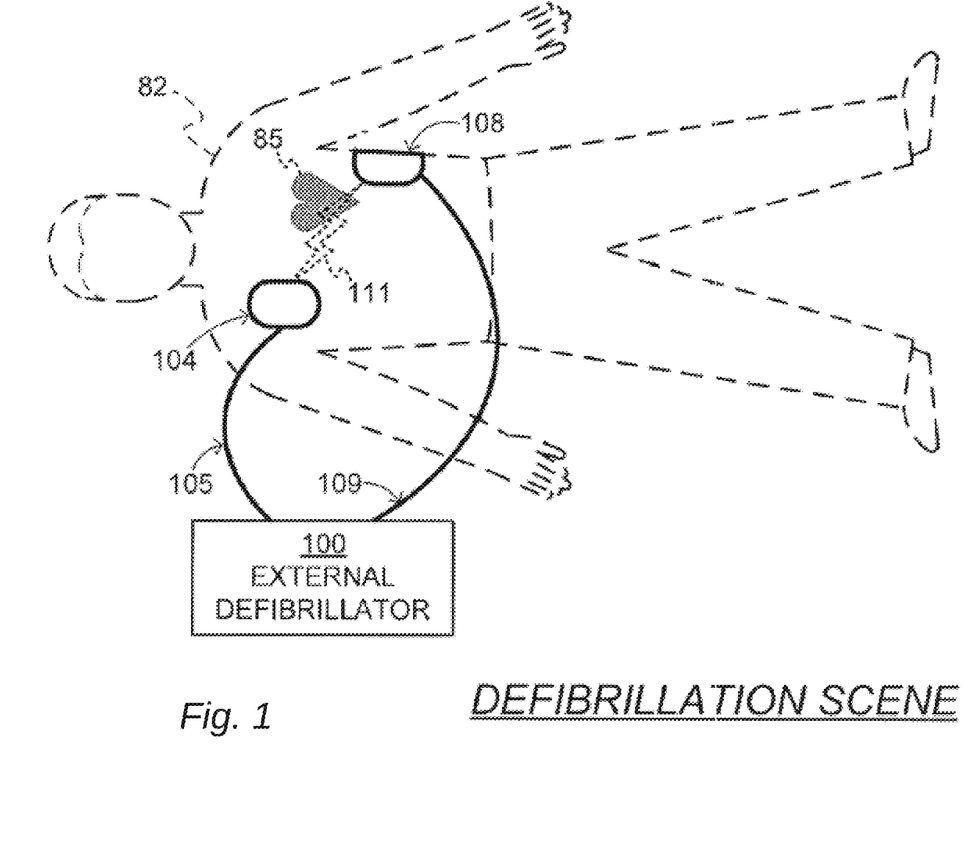
FIG. 1 is a diagram of a scene where an external defibrillator is used to try and save the life of a person in accordance with an embodiment.

FIG. 1 is a diagram of a defibrillation scene. A person 82 is lying supine. Person 82 could be a patient in a hospital, or someone found unconscious and turned on his or her back. Person 82 is experiencing a condition in their heart 85, which could be Ventricular Fibrillation (VF).

A portable external defibrillator 100 has been brought close to person 82. At least two defibrillation electrodes 104, 108 are usually provided with external defibrillator 100. Electrodes 104, 108 are coupled with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111 includes a defibrillation shock, goes also through a heart 85, in an attempt to restart it, for saving the life of person 82. Defibrillator 100 can be one of different types, each with different sets of features and capabilities. The set of capabilities of defibrillator 100 is determined by planning who would use it, and what training a user would be likely to have.

The electrodes 104, 105 may be perishable items with a limited shelf life, which is shorter than the shelf life of the defibrillator 100. For that and other reasons, there may come a time when the electrodes 104, 108 require replacement. However, defibrillator 100 is approved for use only in conjunction with the proper accessories, such as the proper electrodes 104, 108. Accordingly, a mechanism is implemented to confirm that new accessories, such as electrodes 104, 108 are approved for use with the defibrillator 100.

Figure 2:
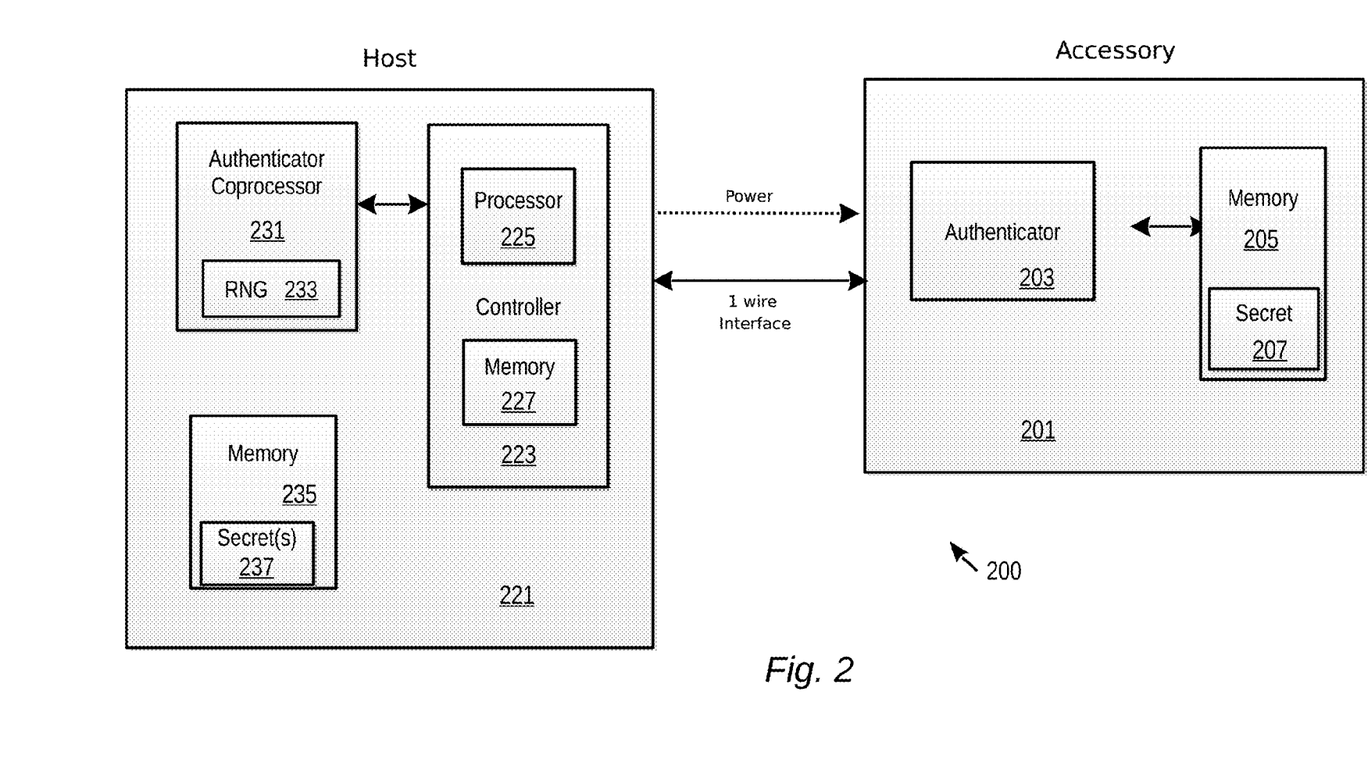
FIG. 2 is a functional block diagram illustrating components of an embodiment of a self-authenticating accessory for a medical device.

FIG. 2 is a functional block diagram generally illustrating an embodiment 200 in which an accessory 201 is configured to authenticate itself to a host medical device 221. Examples of accessory 201 include electrode, probe, point of care labs, video laryngoscope or other device which may be connected to a medical device. Examples of a host medical device 221 include a defibrillator, a monitor, CPR assist device, or the like. The accessory attachment to the host may be either wired or non-wired. For example, in the case of a non-powered accessory, the accessory attachment may be wired. In some non-wired attachments, the accessory may be self-powered. In this embodiment, the accessory 201 includes an authenticator 203 and a memory 205. The memory 205 further includes a "secret" 207.

In this implementation, the authenticator 203 may be a special purpose component configured to perform a secure authentication to a remote device, such as host medical device 221. In this particular implementation, the authenticator 203 is configured to perform a challenge/response type authentication using a shared secret. The secret 207 stored within memory 205 may be a lengthy binary number, hexadecimal number, or other alphanumeric value sufficiently distinct that it is computationally difficult to predict.

The host medical device 221 includes a controller 223, which further includes a processor 225 and a central memory 227. The controller 223 operates in an ordinary manner to perform the normal operations of host medical device 221. For instance, processor 225 retrieves and stores information from and to the central memory 227 in furtherance of the operation of the host medical device 221.

The host medical device 221 also includes an authenticator co-processor 231 and an authenticator memory 235. The authenticator co-processor 231 in this embodiment further includes a random number generator (RNG) 233. The authenticator is configured to perform a secure challenge/response type authentication with a remote device, such as accessory 201, using a shared secret. The authenticator memory 235 includes a data store 237 of one or more secrets. As above, the secret(s) may each be a lengthy binary number, hexadecimal number, or other alphanumeric value sufficiently distinct that it is computationally difficult to predict.

Although numerous different options are available for specific parts, for the sake of disclosure, this embodiment could be implemented using, for example, a "DeepCover Secure Authenticator with SHA-256 Coprocessor and 1-Wire Master Function" (part number DS2465) as the authenticator co-processor 231, and a "DeepCover Secure Authenticator with 1-Wire SHA-256 and 4 Kb User EEPROM" (part number DS28E25) as the accessory authenticator 203. Both parts are available from Maxim Integrated Products, Inc. of San Jose, Calif. One advantage realized by these specific components is the ability to avoid including an additional power connector and to rely on a simple one-wire interface. Another advantage of using a dedicated authentication co-processor on the host medical device 221 is that it reduces the processing overhead on the main processor 225.

Prior to deployment, each of the host 221 and accessory 201 is preprogrammed with at least one shared secret. In one embodiment, when the accessory 201 is manufactured, it is programmed with a given "secret" value (secret 207). The secret 207 could be a value unique to only that one specific accessory 201, or it could be a value unique to a particular model of accessory, or it could simply be a value assigned by the manufacturer and known only to the manufacturer. The secret can be associated with a date or date range so that the manufacturer could discern when the accessory was created by knowing the particular secret programmed into the accessory 201. It should be appreciated that although conceivably possible through extraordinary means, as a practical matter the secret 207 cannot be directly retrieved or read from the accessory 201. In one enhancement, each secret assigned by the manufacturer could also be associated with a feature set for an accessory.

Similarly, when the host medical device 221 is manufactured, it is programmed with at least one, and likely many, authentication secrets. More specifically, as noted above, a manufacturer may assign numerous secrets to numerous accessories (the "possible secrets"). Each possible secret is associated with a particular date or date range and may also be associated with a feature set for a particular accessory.

Figure 3:
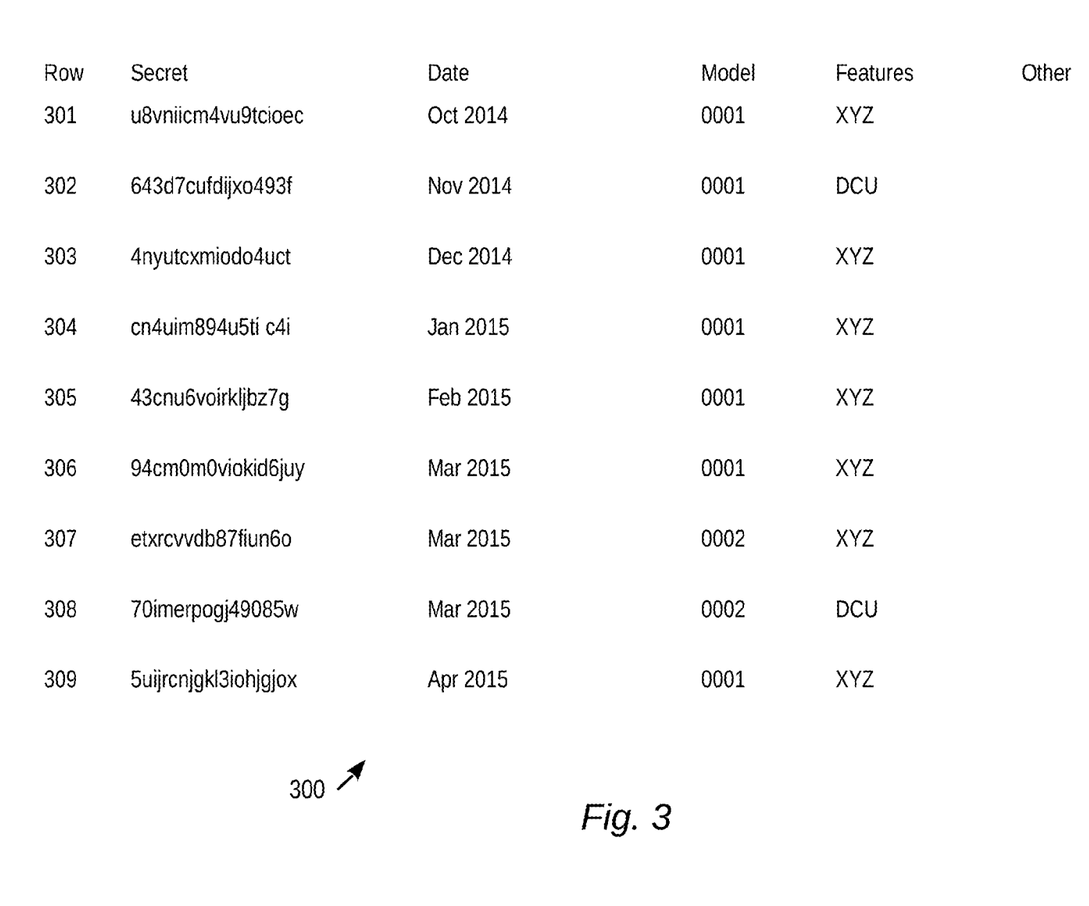
FIG. 3 illustrates a table that includes a number of possible secrets that have been assigned by a manufacturer, in accordance with an embodiment.

For example, and turning briefly to FIG. 3, a table 300 is shown that includes a number of possible secrets that have been assigned by a manufacturer. In its simplest form, each secret is simply a value assigned by the manufacturer to indicate that any accessory containing that value is an authentic product from the manufacturer. In one enhancement, each secret is also associated with at least one date, such as a date of manufacture or a date of expiration. In still further enhancements, each particular secret may also correspond to a particular model of accessory and perhaps even a feature set of that model. For instance, the secret found in row 301 of table 300 may be associated with accessory model 0001, having feature set XYZ, and expiration date of October, 2014. Similarly, the secret found in row 302 also corresponds to accessory model 0001; however, the expiration date for the secret in row 302 is November, 2014 and the feature set is DCU. Thus, an accessory bearing the secret in row 301 will expire roughly one month later than an accessory bearing the secret in row 302.

In some embodiments, table 300 may be preprogrammed at the time of the manufacture of the host medical device 221 with sufficient secrets to last the expected lifetime of the host medical device. In other embodiments, the host medical device 221 may have a smaller table 300 and a communication capability such as wired Internet connectivity, cellular or Wi-Fi connectivity, etc. In one embodiment, the host medical device 221 can determine the current date and based on the expected lifetime of the accessories retrieve additional secrets as needed via the communication capability. In embodiments in which the host medical device 221 is not "connected", the host medical device 221 may include a port such as a USB or Firewire port and be configured to allow manual updates of the table 300 via the port during periodic maintenance of the medical device.

Returning now to FIG. 2, a set of possible secrets is stored in the authentication memory 227 of the host medical device 221. The set that is stored in the host medical device 221 corresponds to accessories that are approved replacements for use with the host medical device 221 (the "valid secrets"). Referring now briefly to both FIG. 2 and FIG. 3, if the host medical device is only compatible with accessory model 0001 but not model 0002, the secrets found in rows 307 and 308 may be omitted from the set of valid secrets stored in the authentication memory 227 of the host medical device 221. Similarly, if the host medical device 221 requires feature set XYZ and is inoperable with an accessory having feature set DCU, the secret found in row 302 may also be excluded from the set of valid secrets stored in the authentication memory 227.

In operation, when a new accessory 201 is attached to the host medical device 221, such as may occur during a replacement, the accessory 201 authenticates itself to the host medical device 221. In one embodiment, such authentication occurs as a challenge/response secure authentication between the authenticator 203 of the accessory 201 and the authenticator co-processor 231 of the host medical device 221.

Although there are numerous acceptable methods for performing a secure challenge/response authentication, for completeness of disclosure, one acceptable method will be described here. In one implementation, the accessory 201 is connected to the host medical device 221, the authenticator co-processor 231 initiates the authentication by providing to the authenticator 203 some seed value, such as a pseudo random value generated by random number generator 233. The seed is considered pseudo random because it may be created in such a manner that it cannot be recreated later. In other words, the pseudo random value may be generated in such a way that it would not be a valid value if created at a later date (e.g., by being partially based on the current date). Such a feature helps reduce the possibility that the challenge/response authentication scheme could be copied and reproduced later by an unauthorized device.

The host medical device 221 provides the seed value to the authenticator 203 of the accessory. The authenticator 203 then creates a Message Authentication Code ("MAC") value based on the seed value from the host in combination with the accessory's stored secret 207. In one particular implementation, the MAC value is created using a hashing algorithm (e.g., the SHA-256 hashing algorithm) on a combination of the seed value and the accessory's stored secret 207. It will be appreciated that the hashing algorithm creates a unique hash value for every different input data. Thus, a hash of the stored secret 207 will always return the same hash value provided the same hashing algorithm is used. However, by hashing a combination of the seed value with the stored secret 207, a different hash value (MAC) will always result so long as the seed values are different.

The authenticator 203 returns the MAC to the host medical device 221. The authenticator co-processor 231 then performs its own hash of the seed value (which the host created) with each of the valid secrets 237 stored in the authentication memory 235. Again, because the authenticator co-processor 231 uses the same hashing algorithm as the authenticator 203, the authenticator co-processor 231 will be able to recreate the same MAC by hashing the known seed in combination with the stored valid secrets 237. If a comparison of the MAC returned from the accessory 201 results in a match with any MAC locally created by the authenticator co-processor 231 from valid stored secrets, then the host medical device 221 accepts that the accessory 201 is an authorized accessory 201. However, if the authenticator co-processor 231 is unable to match the MAC returned from the accessory 201 with any locally-generated MAC using valid stored secrets, then the host medical device 221 rejects the accessory 201 as being unauthorized. In the simplest example, unauthorized could mean that the accessory is simply out of date (expired). Alternatively, unauthorized could mean that the accessory 201 was not manufactured by an authorized manufacturer.

It will be appreciated that very many alternative methods for performing the challenge/response authentication could be implemented. For example, in one alternative, the authenticator 203 could initiate the authentication scheme by volunteering to the host both a seed value which is pseudo randomly generated on the accessory (rather than on the host) with the MAC so that the host need not generate the seed value first. In another alternative (although somewhat less secure), the seed value may be completely randomly generated without regard to repeatability. These and many other alternatives will become apparent to those skilled in the art.

Accordingly, in the embodiment 200 illustrated in FIG. 2, the host medical device 221 can confirm that the accessory 201 is an appropriate replacement without directly reading any stored information on the accessory 201. Rather, the entire authentication process is performed securely and in a way that is not easily spoofed by counterfeiters. In addition, substantially more information (e.g., accessory model number and/or feature set) can be discerned about the accessory based on nothing more than a priori knowledge that corresponds with each stored secret. In some embodiments, in order to reduce cost and complexity, the accessory does not include a memory for storing data accessible by a host, but rather the accessory can include a register or other mechanism to store the secret. For example, in some embodiments the secret can be programmed directly into the authenticator in a tamper-resistant manner.

Another potential advantage of this embodiment is that it would be difficult for an unauthorized dealer to take an expired accessory and modify the secret in the accessory to make the expired accessory appear unexpired. In medical device applications, preventing use of expired accessories can be an important safety concern.

Figure 4:
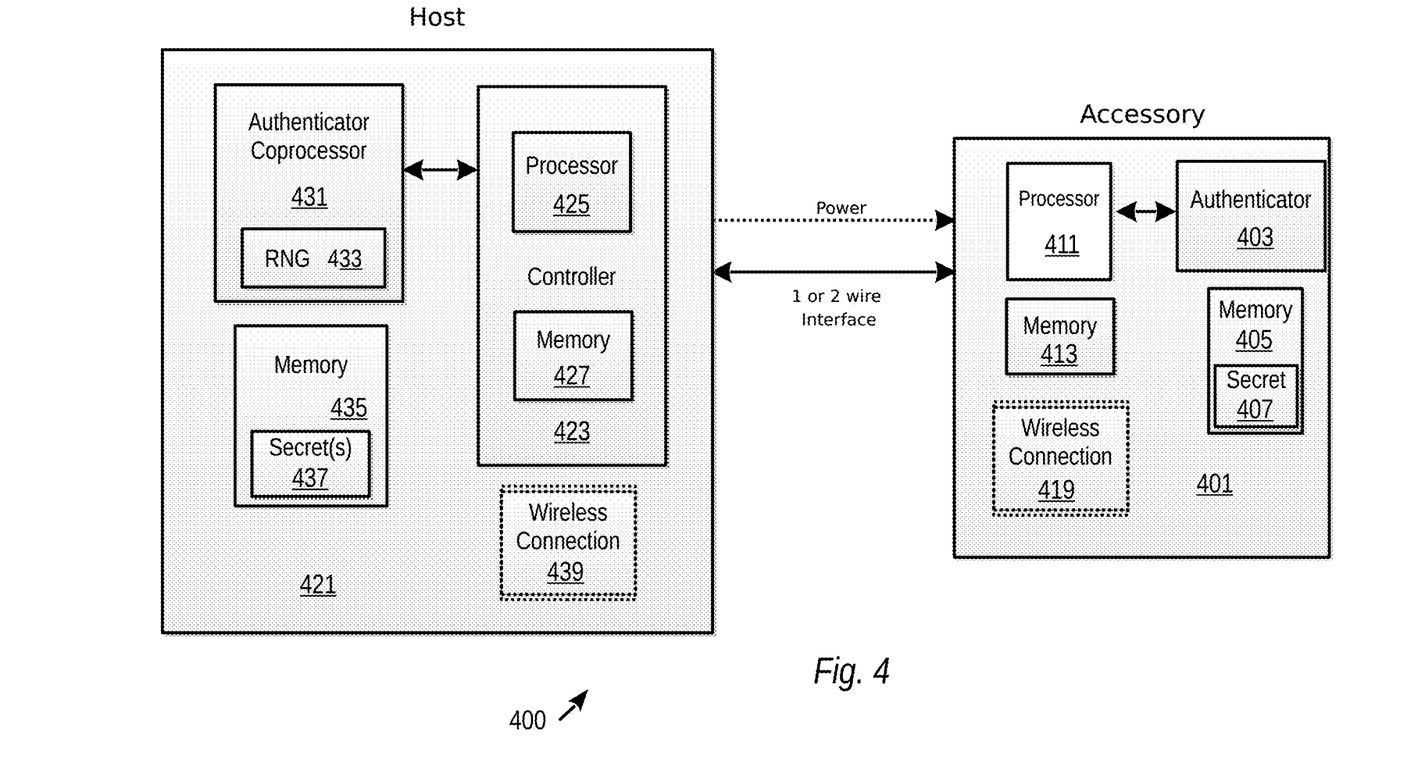
FIG. 4 a functional block diagram generally illustrating an embodiment in which an accessory 401 is configured to authenticate itself to a host medical device.

FIG. 4 is a functional block diagram generally illustrating an embodiment 400 in which an accessory 401 is configured to authenticate itself to a host medical device 421. In the present embodiment 400, the accessory 401 is essentially "smarter" than the accessory 201 of the embodiment illustrated in FIG. 2 by virtue of a microprocessor 411 included directly in the accessory 401 in addition to an authenticator 403. In other words, the embodiment 400 may perform a challenge/response authentication in the manner described above. However, the addition of the microprocessor 411 directly on the accessory 401 enables enhanced functionality beyond (or in addition to) the functionality described in connection with the embodiment 200 shown in FIG. 2.

Shown in FIG. 4 is an optional wireless connection facility embodied as a host wireless connection 439 and an accessory wireless connection 419. These two connections may operate in tandem to enable the host medical device 421 and the accessory 401 to communicate without a wired interface. The wireless connections can operate using any wireless technology, such as Wi-Fi, Bluetooth, cellular (e.g., HSPA or LTE), or the like. Although shown only in FIG. 4, it should be appreciated that the wireless connection facility could equally be implemented in any other embodiment.

The enhanced processing capability of the microprocessor 411 enables intelligent communication between the host medical device 421 and the accessory 401. In one example, a simpler authentication between the host medical device 421 and the accessory 401 may be used merely to confirm the authenticity of the accessory 401 to establish a trusted relationship between the two. Once established, the accessory 401 may perform onboard computations and interact with the host medical device 421 intelligently. For example, a large number of shared secrets that burden the host medical device 421 would not be required. Rather, as few as one shared secret would be necessary to establish that the accessory 401 was in fact authentic and made by or for the manufacturer. Once so authenticated, information received by the host medical device 421 from the accessory 401 could be trusted implicitly, eliminating any need to overload the shared secret with other ancillary information.

Once authenticated, the accessory 401 could simply verify whether it was expired or if it were an appropriate accessory for the host medical device 421. For instance, to verify expiry, the host medical device 421 could simply provide the current date to the processor 411 of the accessory 401. The processor 401 could then query information, such as date of expiration or date of manufacture, stored in a memory 413 on the accessory 401. With that comparison done on the accessory 401, the processor could simply return a yes/no result to the host medical device 421 to confirm whether the accessory 401 has expired or the number of days remaining until expiration. Since the accessory 401 has already been authenticated, the response from the accessory can be trusted by the host medical device 421.

Figure 5:
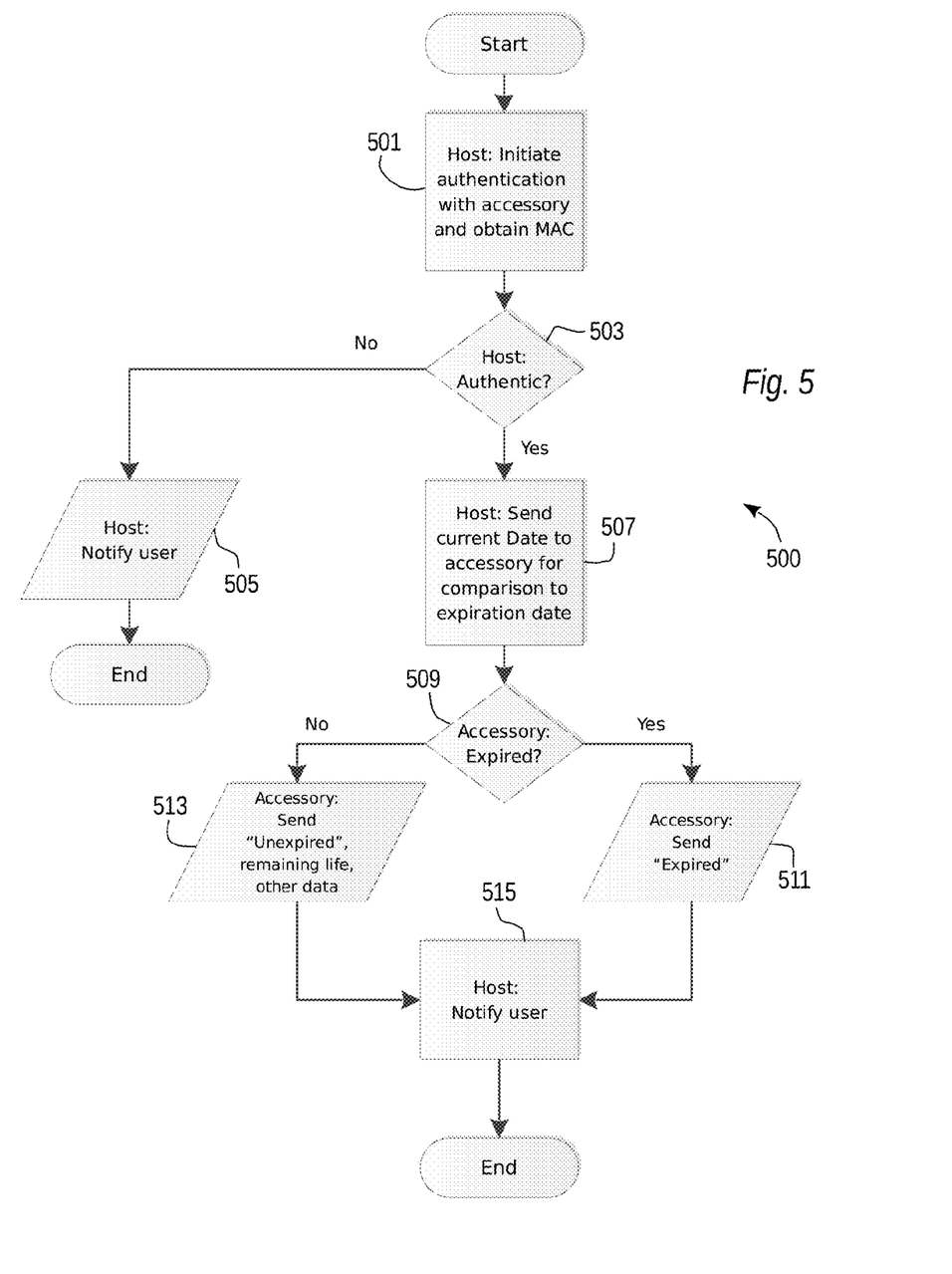
FIG. 5 is a flow chart illustrating a method for performing a verification using the secure challenge and response process of the embodiment illustrated in FIG. 4.

Turning now to FIG. 5, a method 500 is shown to illustrate one example verification, which may be performed using the secure challenge and response process of this embodiment. In summary, (a) host authenticates electrode using secure challenge/response process; (b) if authenticated, host sends current date to accessory; (c) accessory compares current date to expiration date; (d) accessory responds appropriately, such as "expired", "unexpired", the remaining days of "life", etc.

In this exchange the host initiates an authentication with the accessory and computes a message authentication code (MAC) based on data and a secret (step 501). If host cannot verify the MAC (step 503), the authentication fails and the user may be notified (step 505). If the accessory is deemed authentic (step 503) the host will send to the accessory the current date (step 507). The accessory then determines whether the accessory is expired by comparing (step 509) the current date (from the host) with stored information about when it expires or, perhaps, when the accessory was created together with information about how long the accessory is valid. Based on whether the accessory has expired (step 511) or has not expired (step 513), the accessory will report the proper response to the host. The host can notify the user whether the accessory is authentic, expired (if applicable) and other useful data such as, perhaps, preprocessed functionality (step 515). In the event that the accessory is determined to be not authentic, the host medical device may optionally disable certain or all operations that would otherwise make use of the accessory.

Figure 6:
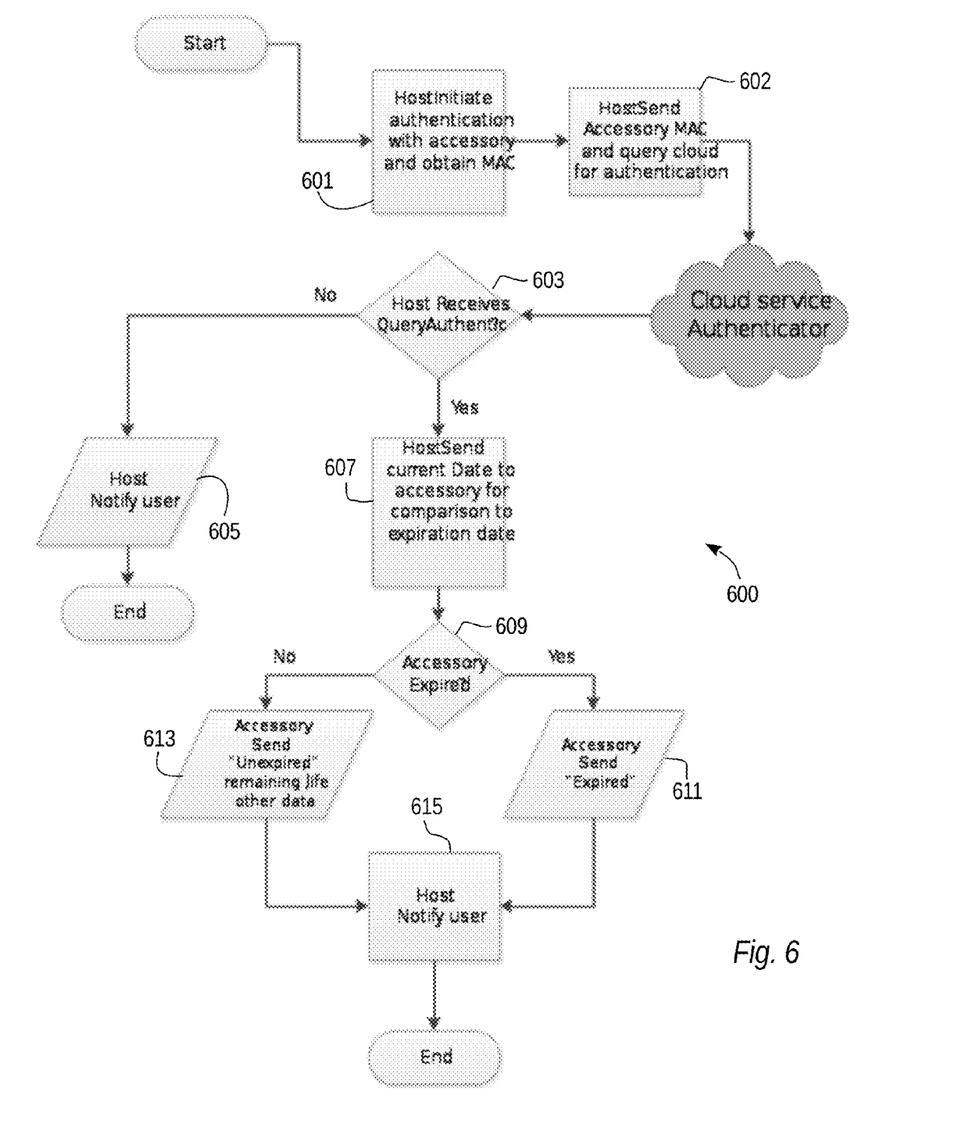
FIG. 6 is a flow chart illustrating another method for performing a verification using the secure challenge and response process of the embodiment illustrated in FIG. 4.

Turning now to FIG. 6, another method 600 is shown to illustrate another example verification, which may be performed using the secure challenge and response process of this embodiment. This method 600 differs from the method 500 shown in FIG. 5 in that at least part of the authentication is performed remotely, such as in the "cloud" or at a remote network location.

In this exchange the host initiates an authentication with the accessory and computes a message authentication code (MAC) based on data and a secret (step 601). In this embodiment, the host transmits the MAC to a cloud-based service to perform the authentication (step 602). The host receives a response from the cloud-based service indicating either that the MAC is authorized or not (step 603). If the response indicates that the authentication fails the user may be notified (step 605). If the response indicates that the accessory is deemed authentic (step 603) the host will send to the accessory the current date (step 607). The accessory then determines whether the accessory is expired by comparing (step 609) the current date (from the host) with stored information about when it expires or, perhaps, when the accessory was created together with information about how long the accessory is valid. Based on whether the accessory has expired (step 611) or has not expired (step 613), the accessory will report the proper response to the host. The host can notify the user whether the accessory is authentic, expired (if applicable) and other useful data such as, perhaps, preprocessed functionality (step 615).

Figure 7:
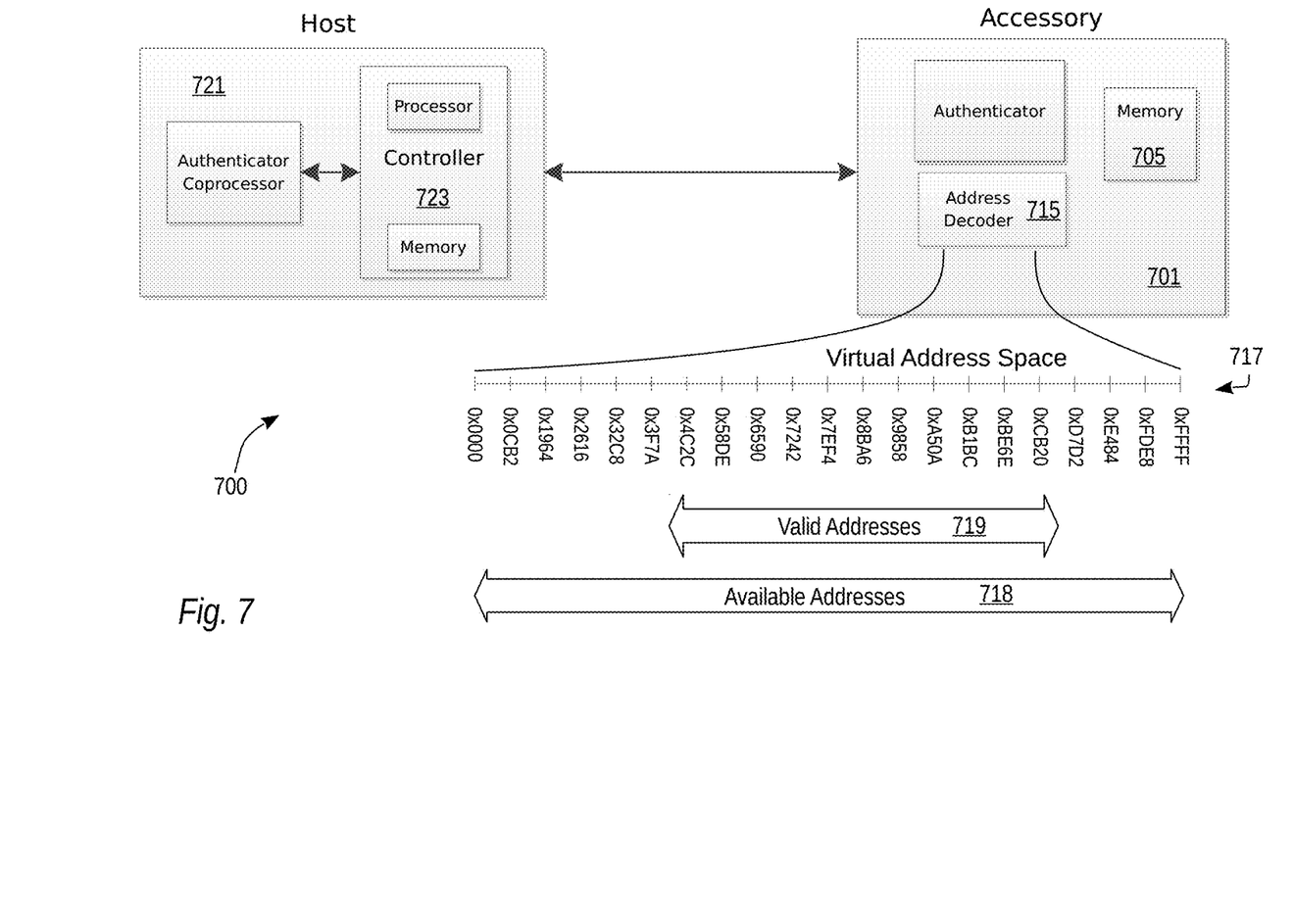
FIG. 7 is a functional block diagram generally illustrating an embodiment in which an accessory is configured to authenticate itself to a host medical device.

FIG. 7 is a functional block diagram generally illustrating a further embodiment 700 in which an accessory 701 is configured to authenticate itself to a host medical device 721. In this third embodiment, the accessory 701 generally operates in a manner similar to either the embodiment 200 shown in FIG. 2 or the embodiment 400 shown in FIG. 4 to authenticate itself to the host medical device 721. However, in this embodiment 700, the host medical device 721 and the accessory 701 employ a form of address decoder 715 to determine whether the accessory 701 is expired. More specifically, once authenticated such that responses returned to the host medical device 721 from the accessory 701 are trusted, the host medical device 721 (via controller 723) posts a pseudo "address" to the address decoder 715. It will be appreciated by those skilled in the art that the "address" may be a value (e.g., binary or hexadecimal) that decodes into a virtual address space wherein the virtual address locations correspond to particular information. Virtual address space mapping, generally, is well known in the art.

In this particular embodiment, the address decoder 715 maps the "address" provided by the host medical device 721 into a virtual address space 717. In one implementation, the entire range of addresses in the virtual address space 717 constitutes the range of possible or available addresses 718 that could be identified by the host medical device 721. However, in this implementation, only a sub space (valid addresses 719) of the available addresses 718 correspond to data which is valid for the accessory 701. A memory 705 may include the data which corresponds to valid addresses 719.

By way of example, the data stored in memory 705 may constitute a range of dates through which the accessory 701 may properly be used. In other words, and conceptually speaking, the available addresses 718 within the virtual address space 717 could represent a range of dates from some given start date until a date in the distant future. The valid addresses 719 may correspond to only those dates for which the accessory 701 is unexpired. Thus, when the accessory 701 is attached to the host medical device 721, the host medical device 721 may post an address value to the address decoder where that address value corresponds to the current date. The address decoder 715 decodes the address value into the virtual address space 717 to determine whether it maps into the valid addresses 718. If not, then the accessory 701 returns an error or other code indicating that the accessory 701 is not valid given the current date. Alternatively, the accessory 701 could compute the difference between the current date and the extent of the valid addresses 718 (i.e., the final valid date) to determine the remaining life of the accessory 701. One potential advantage of this embodiment is that when combined with a conventional authentication scheme, it would be difficult for an unauthorized dealer to take an expired accessory and modify the address decoder 715 to change the expiration date to make the expired accessory appear unexpired. In medical device applications, preventing use of expired accessories can be an important safety concern.

These and other uses and alternatives will become apparent from the foregoing teachings.

In this description, numerous details have been set forth in order to provide a thorough understanding of the described embodiments. In other instances, well-known features have not been described in detail in order to not obscure unnecessarily the description.

A person skilled in the art in view of this description will be able to practice the present invention, which is to be taken as a whole. The specific embodiments disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems. The following claims define certain combinations and subcombinations of elements, features, steps, and/or functions, which are regarded as novel and non-obvious. Additional claims for other combinations and subcombinations may be presented in this or a related document.

What is claimed is:

1. An accessory for a medical device, comprising:
a connector configured for operative communication with the medical device;
a memory configured to store a secret value associated with the accessory, wherein the accessory is configured to prevent the secret value from being retrieved or read from the accessory; and
a processing component capable of communicating, using the connector, to perform a secure authentication of the accessory when the accessory is attached to the medical device, the secure authentication comprising at least a transmission over the connector of a message authentication code (MAC) wherein the MAC is based on, but does not include, the secret value stored in the memory of the accessory, the secure authentication being a challenge and response authentication.

2. The accessory recited in claim 1, wherein the challenge and response authentication is based on a hashing algorithm.

3. The accessory recited in claim 1, wherein the processing component is further configured to receive a seed value over the connector and to perform a hashing function based on, at least, the secret value in combination with the seed value.

4. The accessory recited in claim 3, wherein the seed value is a pseudo random number.

5. The accessory recited in claim 4, wherein the pseudo random number comprises a non-repeating pseudo random number.

6. The accessory recited in claim 1, wherein the secret value comprises information relating to at least one characteristic of the accessory.

7. The accessory recited in claim 6, wherein the at least one characteristic comprises a manufacturing date of the accessory.

8. The accessory recited in claim 6, wherein the at least one characteristic comprises a use-by-date for the accessory.

9. The accessory recited in claim 6, wherein the at least one characteristic comprises a lot number of the accessory.

10. The accessory recited in claim 6, wherein the at least one characteristic comprises a feature set of the accessory.

11. The accessory recited in claim 1, wherein the processing component comprises a microprocessor operative to perform computing operations independent of the medical device.

12. The accessory recited in claim 1, further comprising an address decoder operative to map an input address value into a virtual address space, at least a subset of addresses in the virtual address space corresponding to data confirming the validity of the accessory.

13. The accessory recited in claim 6, wherein the at least one characteristic comprises a date indicative of the expiration date of the accessory.

14. The accessory recited in claim 1, wherein the connector is configured for either wired communication, wireless communication, or both wired and wireless communication.

15. The accessory recited in claim 1, wherein the secure authentication is performed without a user of the medical device knowing the secret value and MAC.

16. The accessory recited in claim 1, wherein the accessory, when connected to the medical device via the connector, is configured to interoperate with the medical device to perform a medical function on a patient.

17. The accessory recited in claim 16, wherein the medical function comprises sensing a physiological parameter of the patient.

18. The accessory recited in claim 16, wherein the medical function comprises providing a medical treatment to the patient.

19. An accessory for a medical device, comprising:
 means for storing a shared secret that is associated with the accessory, wherein the accessory is configured to prevent the shared secret from being retrieved or read from the accessory;
 means for receiving a request to authenticate the accessory to the medical device, the authentication being based on the shared secret, the shared secret corresponding to information that verifies the accessory may be used with the medical device; and
 means for transmitting to the medical device a message authentication code (MAC) based on the shared secret without transmitting any stored information from the accessory to the medical device.

20. The accessory recited in claim 19, wherein the authentication comprises a challenge and response procedure.

21. The accessory recited in claim 19, wherein the information that verifies the accessory may be used with the medical device comprises an expiration date for the accessory.

22. The accessory recited in claim 19, wherein the shared secret corresponds to a manufacturer of accessories authorized to operate with the medical device.

23. The accessory recited in claim 19, further comprising means for receiving from the medical device an address value corresponding to a virtual address space; and means for transmitting a response indicative of whether the address value falls within a valid range of virtual addresses for the accessory.

24. The accessory recited in claim 19, further comprising, means for reducing the functionality of the accessory if the message authentication code does not correspond to an authorized accessory.

25. An accessory for a medical device, comprising:
 a first connector configured for operative communication with the medical device;
 a second connector, coupled to the first connector, configured for operative communication with one or more replaceable electrodes; and
 a component capable of communicating with the medical device, using the first connector, to perform a secure authentication of the accessory when the accessory is attached to the medical device, the authentication comprising at least a transmission over the connector of a message authentication code (MAC) wherein the MAC is based on, but does not include, information available at the accessory, the authentication being a challenge and response authentication, wherein the accessory is configured to prevent the information available at the accessory from being retrieved or read from the accessory.

26. The accessory recited in claim 25, where the accessory is further configured to provide information used by the medical device to determine whether the one or more replaceable electrodes are in condition for use.

27. The accessory recited in claim 25, wherein the accessory is further configured to provide information used by the medical device to determine if the one or more replaceable electrodes is expired.

28. The accessory recited in claim 19, further comprising means for inter-operating with the medical device if the message authentication code confirms that the accessory is authorized to operate with the medical device.

* * * * *

UNITED STATES PATENT AND TRADEMARK OFFICE
CERTIFICATE OF CORRECTION

PATENT NO. : 9,916,436 B2
APPLICATION NO. : 14/523727
DATED : March 13, 2018
INVENTOR(S) : Matthew L. Bielstein It is certified that error appears in the above-identified patent and that said Letters Patent is hereby corrected as shown below:

Column 10, Line 27, Claim 25, "fora" should read --for a--

Signed and Sealed this
Second Day of October, 2018

Andrei Iancu
*Director of the United States Patent and Trademark Office*